(12) United States Patent
Shives et al.

(10) Patent No.: US 6,871,560 B2
(45) Date of Patent: Mar. 29, 2005

(54) ELECTRODE INSPECTION SYSTEM

(75) Inventors: Gary D. Shives, Brunswick, OH (US);
Paul S. Sirocky, Brook Park, OH (US);
Thomas E. Michaels, Tucker, GA (US)

(73) Assignee: UCAR Carbon Company Inc.,
Wilmington, DE (US)

( * ) Notice: Subject to any disclaimer, the term of this patent is extended or adjusted under 35 U.S.C. 154(b) by 113 days.

(21) Appl. No.: 10/076,946

(22) Filed: Feb. 14, 2002

(65) Prior Publication Data

US 2002/0148295 A1 Oct. 17, 2002

Related U.S. Application Data

(60) Provisional application No. 60/268,952, filed on Feb. 15, 2001.

(51) Int. Cl.[7] ............................................. G01N 9/24
(52) U.S. Cl. .......................... 73/866; 73/633; 73/641
(58) Field of Search ......................... 73/866, 633, 635,
73/640, 641; 310/328; 376/249, 245, 248;
901/45

(56) References Cited

U.S. PATENT DOCUMENTS

| | | | | |
|---|---|---|---|---|
| 3,780,570 A | | 12/1973 | Collins ..................... 73/67.5 R |
| 4,312,230 A | * | 1/1982 | Bricker et al. ................ 73/638 |
| 4,554,834 A | | 11/1985 | Prinz et al. .................... 73/597 |
| 5,031,458 A | * | 7/1991 | Young et al. ................. 73/636 |
| 5,404,755 A | | 4/1995 | Olson et al. .................. 73/639 |
| 5,719,337 A | * | 2/1998 | Hall et al. ..................... 73/597 |
| 5,770,913 A | * | 6/1998 | Mizzi .......................... 310/328 |
| 5,814,731 A | | 9/1998 | Alexander et al. ............ 73/644 |
| 5,857,534 A | * | 1/1999 | DeVault et al. ............... 180/21 |
| 5,996,413 A | | 12/1999 | Iyer et al. ..................... 73/592 |
| 6,138,515 A | | 10/2000 | Moufle et al. ................ 73/639 |
| 6,459,748 B1 | * | 10/2002 | Everett et al. ............. 376/249 |
| 6,460,414 B1 | * | 10/2002 | Erickson et al. ............. 73/603 |
| 6,484,583 B1 | * | 11/2002 | Chennell et al. ............. 73/623 |

OTHER PUBLICATIONS

Exhibit "A", drawing of commercially used predecessor to present invention.
Exhibit "B", FANUC Robotics North America, Inc., 1999, brochure describing the S-430i robots.

* cited by examiner

Primary Examiner—Hezron Williams
Assistant Examiner—Jacques M. Saint-Surin
(74) Attorney, Agent, or Firm—Waddey & Patterson, P.C.; James R. Cartiglia

(57) ABSTRACT

A system is provided for ultrasonic inspection of cylindrical carbon articles, such as electrodes of the type utilized in electric arc steel making furnaces. An inspection station is provided for receiving the electrode in a fixed longitudinal location and for rotating the electrode about the longitudinal axis of the electrode. Master and slave robots are provided, and each carries a pair of transducers arranged to engage the electrode at circumferentially spaced positions about the electrode. Each pair of transducers is carried on a yoke. The inspection station rotates the electrode while the master and slave robots o each carry their associated pair of transducers along approximately one half the length of the electrode.

14 Claims, 10 Drawing Sheets

ELECTRODE INSPECTION SYSTEM

This application claims benefit of our now abandoned U.S. provisional patent application Ser. No. 60/268,952 filed Feb. 15, 2001.

BACKGROUND OF THE INVENTION

1. Field of the Invention

The present invention relates generally to automated inspection systems for cylindrical carbon articles, especially graphite electrodes.

2. Description of the Prior Art

The current technology in the manufacture of steel from recycled scrap steel materials is highly dependent upon the use of electric arc furnaces wherein the steel scrap and other material is melted by a high energy electric arc. One critical component utilized in an electric arc furnace is a column of large carbon electrodes. These carbon electrodes are generally cylindrical in shape with integral threaded pin and box connections on either end. The cylindrical carbon electrodes typically have diameters in the range of 15 to 30 inches, and typically have lengths ranging up to about ten feet.

The carbon electrodes are used up during the steel making process in an electric arc furnace. Essentially, the end of the electrode burns away during the steel making process. The electrodes are placed in the furnace as a threaded column of electrodes, and as the lowermost electrode burns away the column of electrodes is advanced and periodically a new electrode segment is added to the top end of the column.

In addition to the expected burning away at the lower end of the electrode, due to the extreme environmental conditions within the steel making furnace, the electrodes sometimes suffer a more rapid and undesired consumption rate due to physical non-conformities in the electrode. Examples are cracks and the like, which may cause chunks of the electrode to separate, thus increasing the rate of usage of the electrode and decreasing the life of the electrode and its effectiveness.

There is, therefore, a need for a quality control technique to provide nondestructive testing of electrodes to identify internal defects which are not otherwise observable. Such systems can be utilized as a monitor on the manufacturing process to improve the various process parameters, thus resulting in an improved work product as a batch of carbon electrodes is manufactured. Such an inspection system can also be utilized to detect and eliminate unsatisfactory product prior to delivery to the customer who will use the same in an electric arc furnace. In addition, the system can be used to correlate internal electrode structures with manufacturing process parameters and product performance to identify superior process parameters.

A predecessor of the present invention has been utilized, which is a much more rudimentary system for testing of the type just described. The predecessor system provided a cradle for receiving the carbon electrode to be tested. The carbon electrode was moved onto the cradle by movement in a transverse direction perpendicular to the length of the carbon electrode. A single pair of roller transducers was then positioned on opposite sides of the electrode through the use of two separate transducer placement mechanisms. During the testing operation, the roller transducers were each simultaneously moved along the entire length of the electrode to be tested. The roller transducers generated an axial topographic scan image of the electrode. The roller transducers were then disengaged and removed from the carbon electrode, which was picked up from the cradle and again moved in a direction transverse to the length of the electrode to remove it from the test cradle.

While the predecessor system was operable to perform the general type of inspection which is the subject of the system of the present invention, it was not capable of operating at sufficient capacity to provide the volume of testing desired.

Accordingly, there is a need for an improved testing system of the type generally described providing improved systems for handling of the electrodes in order to allow testing of a high volume of carbon electrodes, such as would be manufactured by a modern electrode manufacturing plant.

SUMMARY OF THE INVENTION

The present invention provides an improved system for inspection of generally cylindrical carbon electrodes. The invention may also be used for handling and inspection of other large cylindrical carbon articles.

In one aspect of the invention, an improved robotic inspection system is provided for placement of the inspection transducers about the carbon electrode which is to be tested. The robotic inspection system includes a yoke having first and second spaced branches. A robotic arm assembly has the yoke attached thereto. The arm assembly is movable between an operating position wherein the yoke is received about the electrode, and a withdrawn position wherein the yoke is removed from the electrode. A pair of roller transducers are attached to the first and second branches of the yoke, respectively, and are arranged to operatively interact with the electrode at circumferentially spaced positions about the electrode when the robotic arm assembly is in its operating position.

In another aspect of the invention, the system just described includes a second such robotic arm assembly carrying a second yoke and a second pair of transducers. The first and second robotic arm assemblies are master and slave, respectively, and are constructed to move in synchronization with each other. When the first and second robotic arm assemblies are in their operating position with the first and second yokes received about the electrode, the first and second yokes are spaced by a distance equal to approximately one half of a length of the electrode which is to be inspected, so that each yoke can simultaneously traverse about half of the length to be inspected.

In another aspect of the invention, the inspection system includes a rotator station for receiving the electrode in a fixed longitudinal location and for rotating the electrode about the longitudinal axis of the electrode while the electrode is in the fixed longitudinal location. A master robot including a first pair of transducers is arranged to engage the electrode at circumferentially spaced positions about the electrode. A slave robot is constructed to move in synchronization with the master robot, including a second pair of transducers arranged to engage the electrode at a location longitudinally spaced from the first pair of transducers, so that the first and second pairs of transducers may simultaneously scan first and second portions, respectively, of the length of the electrode.

In another aspect of the invention, the inspection system just described including the rotator station, includes a conveyor system having electrode path in line with the longitudinal axis of the electrode at the rotator station. Additionally, the rotator station preferably includes an elevator for placing the electrode on a set of powered rotational rollers, and for raising the electrode from the powered rotational rollers. Thus, the cylindrical carbon electrodes move in a linear path and the inspection station is aligned with and is part of that linear path of the manufacturing operation.

In still another aspect of the present invention, a method is provided for inspecting cylindrical carbon electrodes for internal physical defects. The method includes the steps of:

(a) placing first and second pairs of transducers at first and second longitudinally spaced locations along a length of the electrode, and with the transducers of each pair being spaced from each other about a circumference of the electrode;

(b) rotating the electrode about its longitudinal axis; and (c) during step (b), providing relative longitudinal movement between the electrode and the first and second pairs of transducers, so that the first and second pairs of transducers simultaneously scan first and second portions of the length of the electrode.

It is therefore a general object of the present invention to provide improved systems for inspection of cylindrical carbon articles, including but not limited to electrodes.

Another object of the present invention is to provide a system which can inspect carbon articles at increased speed by utilizing multiple sets of transducers which simultaneously scan multiple portions of a length of the article, thus, reducing the scanning time as compared to that which would be required to scan the article with a single pair of transducers.

Another object of the present invention is the provision of an inspection system wherein the carbon articles move in a linear path parallel to a longitudinal axis of the article, as the articles move through an inspection station.

Other and further objects, features and advantages of the present invention will be readily apparent to those skilled in the art upon a reading of the following disclosure when taken in conjunction with the accompanying drawings.

BRIEF DESCRIPTION OF THE DRAWINGS

FIG. 1 shows a series of electrodes on a manufacturing line, moving in an axial path from left to right through in inspection station. At the inspection station, a master and a slave robot are shown on opposite sides of the electrode for engaging the electrode with two pairs of inspection transducers.

FIG. 2 shows an empty inspection station with both of the robot assemblies fully withdrawn from the inspection station, and with a cylindrical carbon electrode located upstream of the inspection station and about to move along the conveyor system into the inspection station.

In FIG. 3, the carbon electrode has moved into the inspection station. The elevators of the inspection station are still in the raised position. The robots have swung their yokes with their corresponding pairs of transducers into a position above the electrode.

In FIG. 4, the elevators have lowered the electrode onto the supporting drive rollers and the yokes carried by the robots have pivoted downward to place their pairs of roller transducers in an initial position at which the scan would be begun. The yokes are spaced by a distance equal to approximately one half the length of the electrode which is to be scanned.

FIG. 5 illustrates the position of the robots and the roller transducers at the end of a scan. Each pair of transducers has scanned approximately one half the length of the electrode as they move between their position of FIG. 4 to their position of FIG. 5.

In FIG. 6, the scan has been completed and the yokes carried by the robots have pivoted back to an upward position out of engagement with the electrode.

In FIG. 7, the robots are continuing to swing their yokes away from the inspection station.

In FIG. 8, the elevators have raised the electrode back up to a position in line with the discharge conveyor, and the electrode is beginning to move out of the inspection station onto the discharge conveyor.

In FIG. 9, the electrode has moved completely out of the inspection station and is moving down the discharge conveyor downstream of the inspection station. The robots have swung their yoke assemblies still further away from the inspection station. The robots will continue to swing to the fully removed position like that of FIG. 2 and another electrode will move into the inspection station, thus beginning the process anew as illustrated in FIG. 2.

DETAILED DESCRIPTION OF THE PREFERRED EMBODIMENTS

Figure 1:
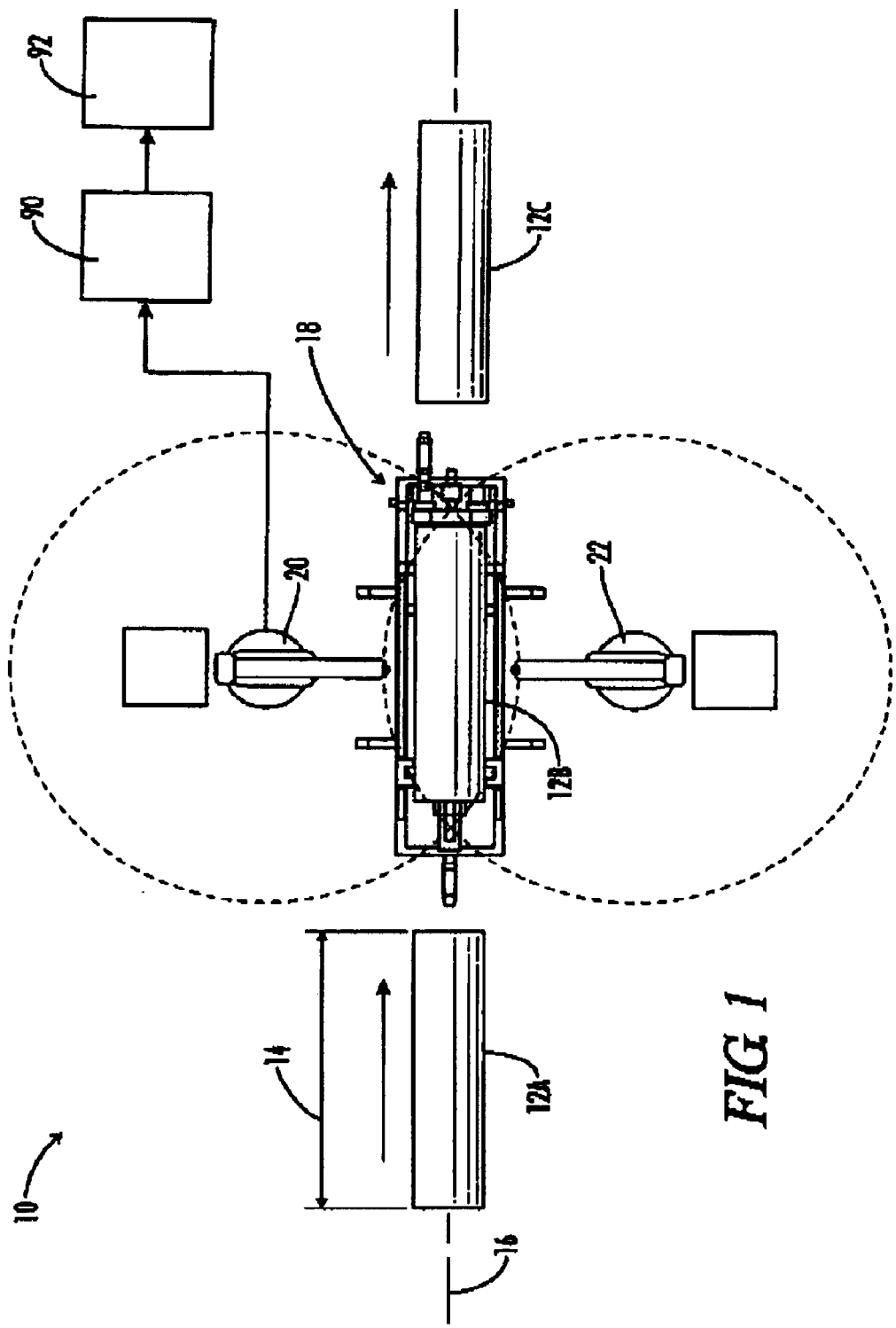
FIG. 1 is a schematic plan view of an electrode inspection system in accordance with the present invention.

Referring now to the drawings, and particular to FIG. 1, the apparatus or system for inspection of a cylindrical carbon electrode is shown and generally designated by the numeral 10.

In FIG. 1, a series of cylindrical carbon electrodes 12A, 12B and 12C, are shown. The system 10 includes inspection station 18. The first carbon electrode 12A is upstream of the inspection station 18. The second carbon electrode 12B is in place in the inspection station 18. The third carbon electrode 12C has already moved through the inspection station 18, and is now downstream of the inspection station.

A master robot 20 and a slave robot 22 are located on opposite sides of the inspection station 18. The robots 20 and 22 may, for example, be Fanuc Model S-430i robots available from Fanuc Robotics North America of Rochester, Mich. These robots provide six axes of motion. The S-430i model is a 118 inch reach robot with a payload capacity of 275 lbs.

The details of construction of the system 10, including the inspection station 18 and the master and slave robots 20 and 22 are best seen in the perspective views of FIGS. 2–9.

In FIG. 1, the suffixes A, B and C are merely used for ease of reference to the three cylindrical electrodes shown in series. In the remaining FIGS. 2-9 where only a single electrode is illustrated in order simplify the illustration, the electrode is simply identified by the numeral 12.

Each electrode 12 has a length 14 and a longitudinal axis 16 parallel to the length 14. In FIG. 1, the electrodes 12 A, B and C are schematically drawn, and no attempt has been made to illustrate the pin and box ends thereof. In FIGS. 2–9, each electrode is shown in more detail, including a pin end. It will also be understood by those skilled in the art that electrodes are sometimes manufactured with two box ends and with a separate pin connector which will be placed between and connect adjacent electrodes when the same are assembled in an electrode string in an electric arc furnace.

In FIGS. 2–9, conveyor system 24 is schematically represented by a plurality of V-shaped supports. Conveyor system 24 includes a downstream portion 26, an inspection station portion 28. and an upstream portion 30. Each V shaped member 24 is schematically representative of a pair of V shaped rollers within which one of the cylindrical electrode segments 12 may be cradled. The electrodes 12 may be moved along the length of the conveyor system 24 in a direction parallel to the longitudinal axis 16 of the electrode segments 12 by any conventional conveyor power system. For example, one or more of the V shaped roller members 24 may be driven support rollers which can selectively advance the electrodes along the path of the conveyor system. Any other conventional conveyor system could also be utilized. For example, a belt conveyor could be used.

The inspection station portion 28 of the conveyor system 24 also includes as an elevator 32. Each of the V shaped support portions 28 can be lowered from the position shown in FIGS. 2 and 3 to the position shown in FIG. 4 wherein the electrode 12 has been brought to rest upon two spaced pairs of powered rotational rollers 34A and 34B which as further described below will be utilized to rotate the electrode 12 about its longitudinal axis 16 during the inspection process.

The inspection station 18 can be generally described as inspection station 18 for receiving the electrode 12 in a fixed longitudinal location, such as that illustrated in FIGS. 3–7, and for rotating the electrode 12 about its longitudinal axis 16 while the electrode 12 is in the fixed longitudinal location.

The powered rotational rollers 34 include first and second longitudinally spaced pairs 34A and 34B. At least one of the pairs of rollers 34A or 34B is attached to a motorized positioning slide 35 longitudinally movable relative to the other in order to accommodate different lengths of electrodes 12.

The elevator 32 provides a system for placing the electrode 12 on the powered rotational rollers 34A and 34B and for raising the electrode 12 from the powered rotational rollers 34A and 34B.

As noted, the inspection station 18 includes an intermediate section 28 of the V-roller conveyor 24. This conveyor section 28 is powered and includes a retractable stop roller 29 with an electrode sensing switch. The electrode 12 enters the inspection station 18 from the upstream portion 30 of the conveyor 24. The forward pair 34B of rotational rollers will preferably be slighted canted to force the electrode into a positive stop at the forward end of the inspection station. The conveyor drive rollers position the electrode against the stop roller 29 which is in its raised position in FIG. 2, and then the electrode 12 is lowered approximately twelve inches by elevators 32 onto the rotational rollers 34A and 34B. After testing is complete, the V-rollers 28 will elevate to pickup the electrode 12 off the rotational rollers 34A and 34B, and place the electrode 12 at the elevation of the exit portion 26 of the conveyor 24. The stop roller 29 is retracted, and the electrode 12 is moved onto the exit 26 portion of the conveyor 24.

Each of the master and slave robots 20 and 22 is constructed in a similar fashion. The following description is provided for the slave robot 22 which is in o the foreground of FIGS. 2–9 and is the most easily described.

Slave robot 22 has a base 36. A turntable 38 is mounted upon the base 36 and rotates about a vertical axis. A drive system 39 is carried on the turntable 38 and drives the robot 22. A robotic arm assembly 40 includes a pivotal shoulder connection 42 to the turntable 38. The arm assembly 40 includes a main arm 44 and a forearm 46 joined at a pivotal elbow connection 48. The forearm member 46 carries a wrist mechanism 48.

Figure 8:
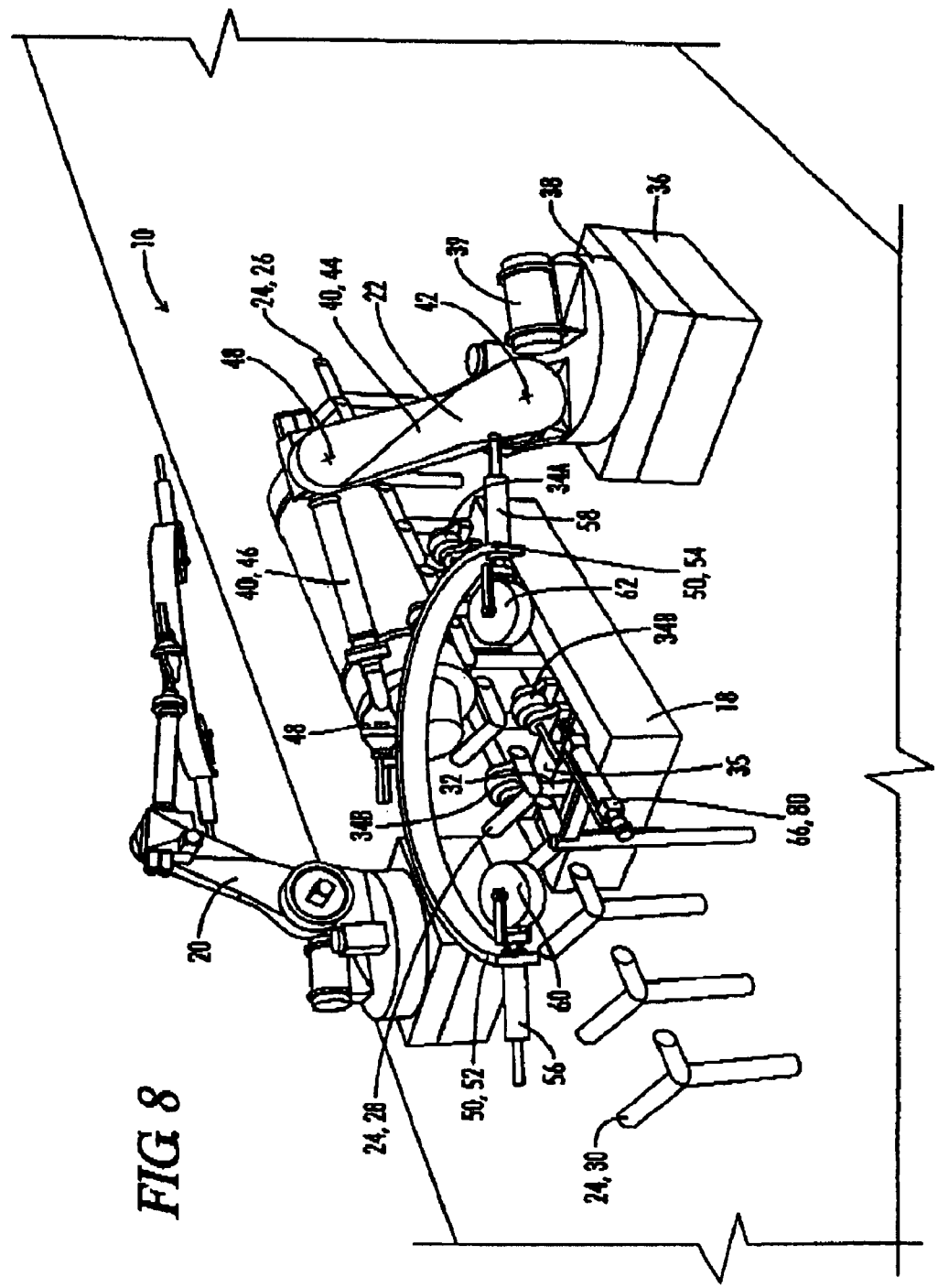
Figure 9:
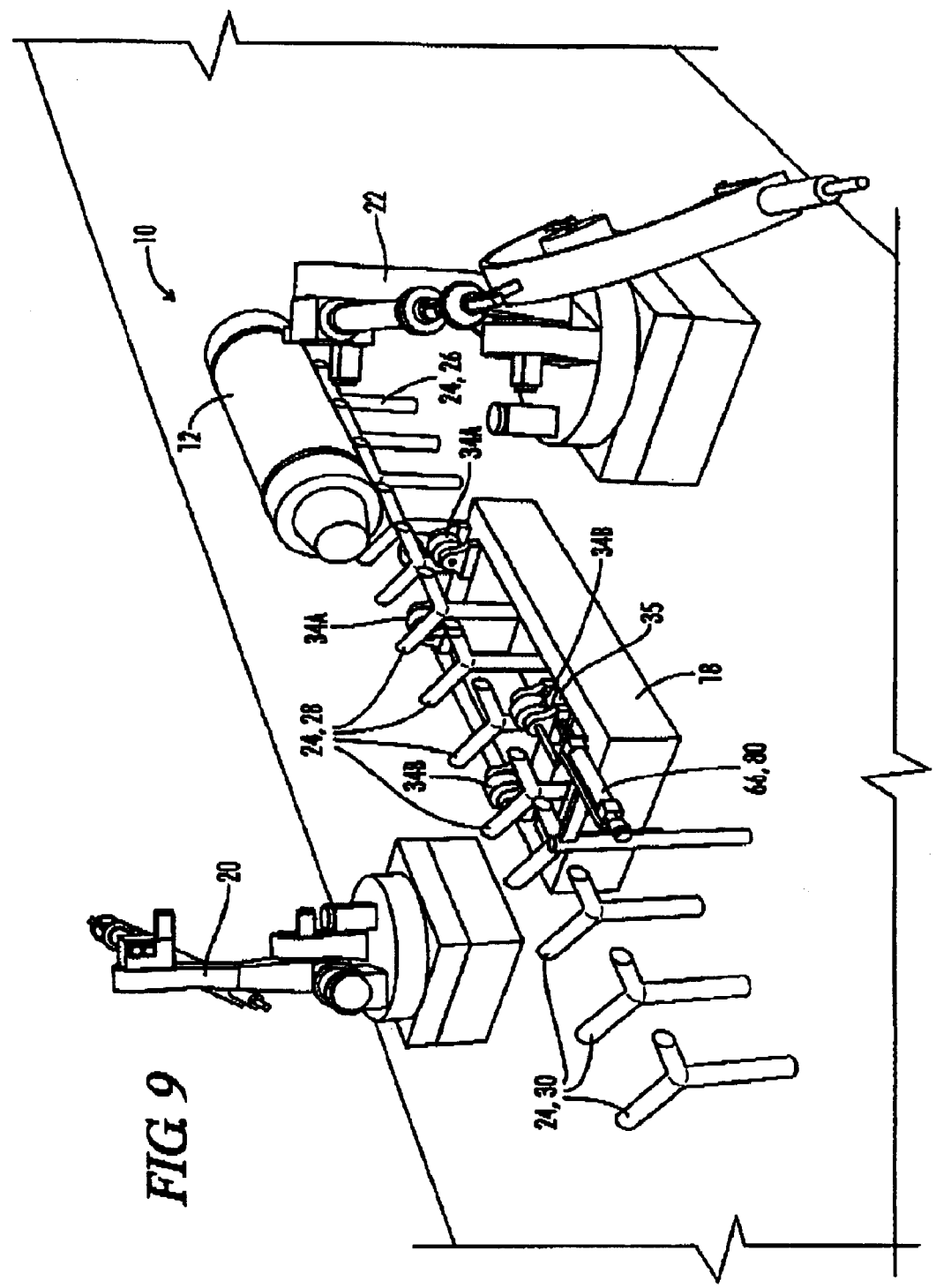

As best seen in FIG. 8, a yoke 50 is attached to the wrist mechanism 48 of robotic arm assembly 40. The yoke includes first and second spaced branches 52 and 54 on opposite sides of the connection to wrist mechanism 48.

Pneumatic cylinders 56 and 58 are attached to the outer ends of first and second branches 52 and 54, respectively. Pneumatic cylinders 56 and 58 in turn support a pair of transducers 60 and 62. The transducers 60 and 62 are roller transducers, the details of which are further shown in FIG. 10. Each pair of transducers 60 and 62 with its respective yoke 50 and pneumatic cylinders 56 and 58 is arranged to operatively interact with the electrode 12 at circumferentially spaced positions about the electrode 12 when the robotic arm assembly 40 is moved to its operating position, such as illustrated in FIGS. 4 and 5.

The pneumatic cylinders 56 and 58, which may also be referred to as extendable rams, allow their respective transducers to be extended toward and retracted from the electrode 12 as necessary during the placement or removal of the transducers from engagement with the electrode 12. Preferably, as is illustrated in FIGS. 4 and 5, the transducers 60 and 62 are arranged to engage the electrode 12 on diametrically opposite sides thereof. When the transducer roller 60 and 62 are engaged with the electrode 12 as shown in FIGS. 4 and 5, each roller transducer is rotatable about an axis generally parallel to the length 14 of electrode 12 and parallel to the longitudinal axis 16 of electrode 12.

Figure 3:
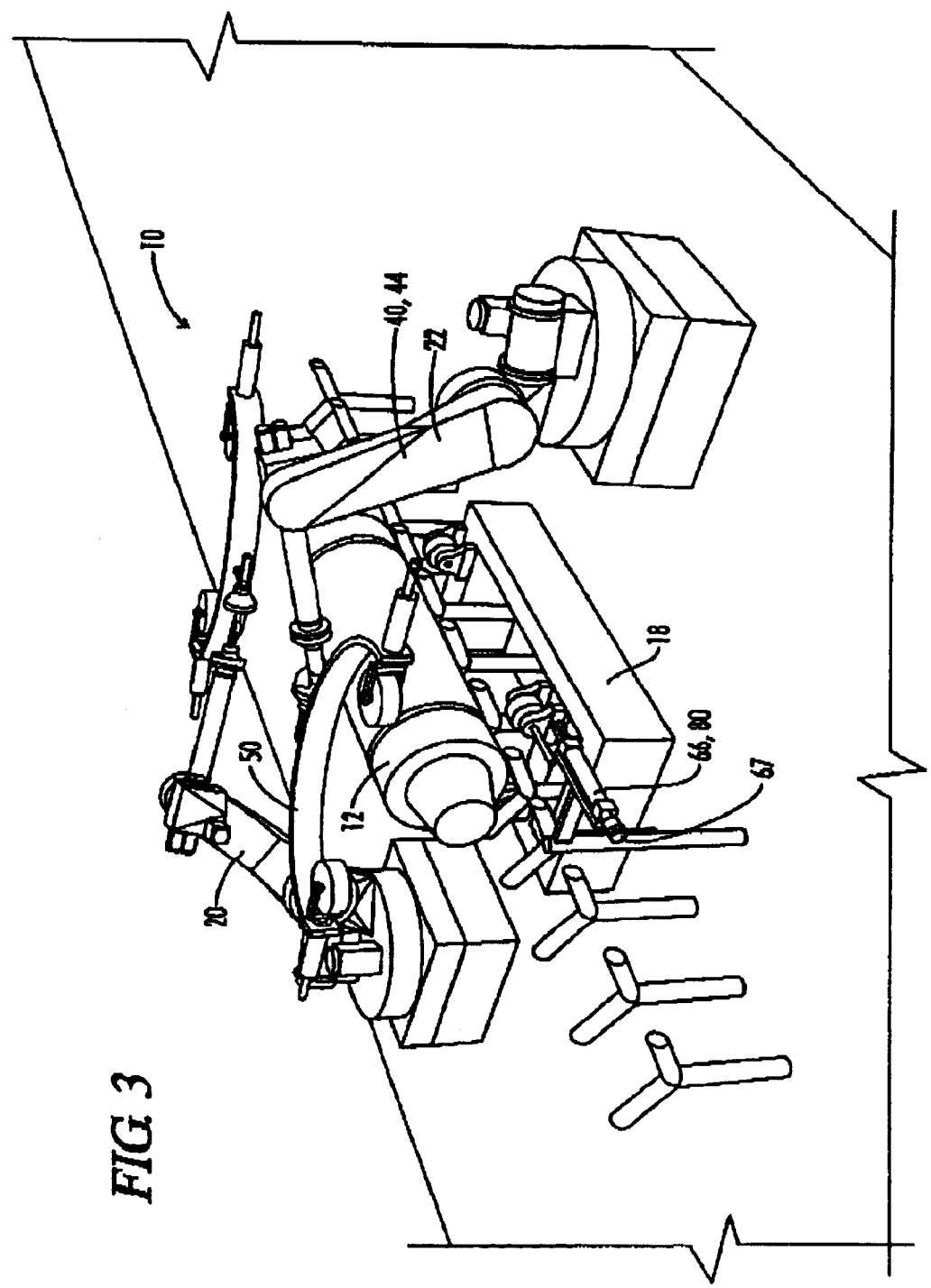
Figure 4:
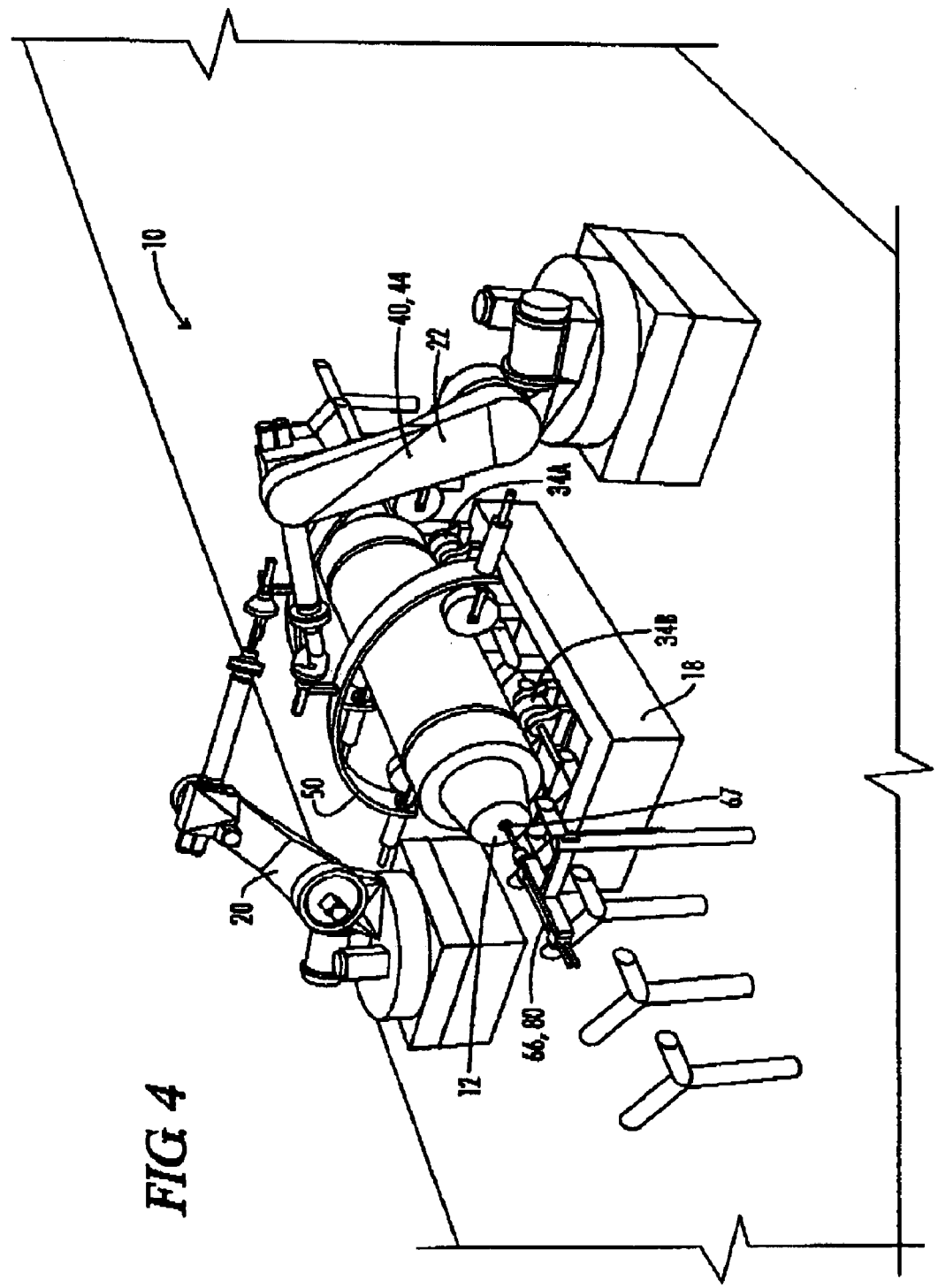
Figure 5:
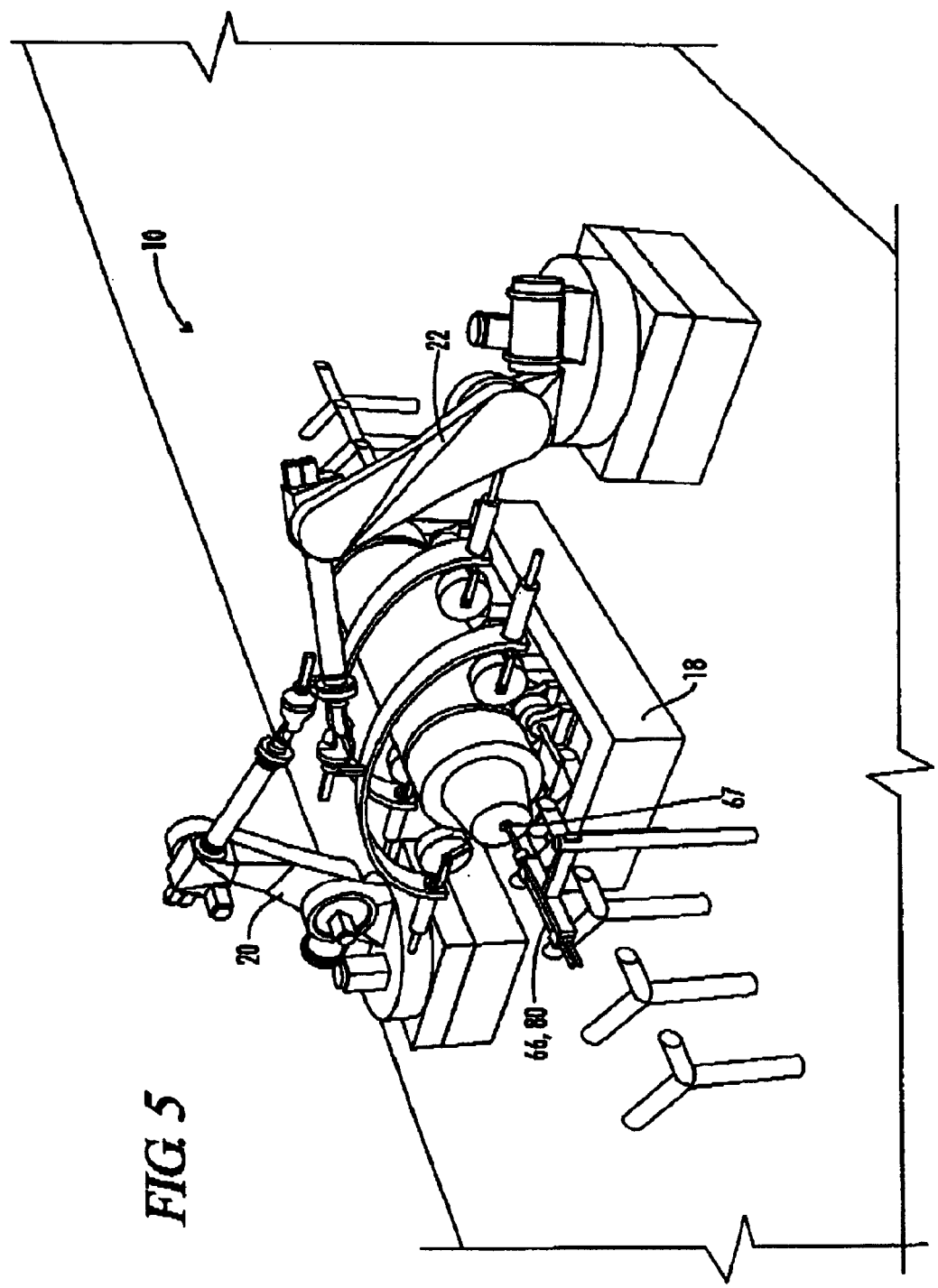
Figure 6:
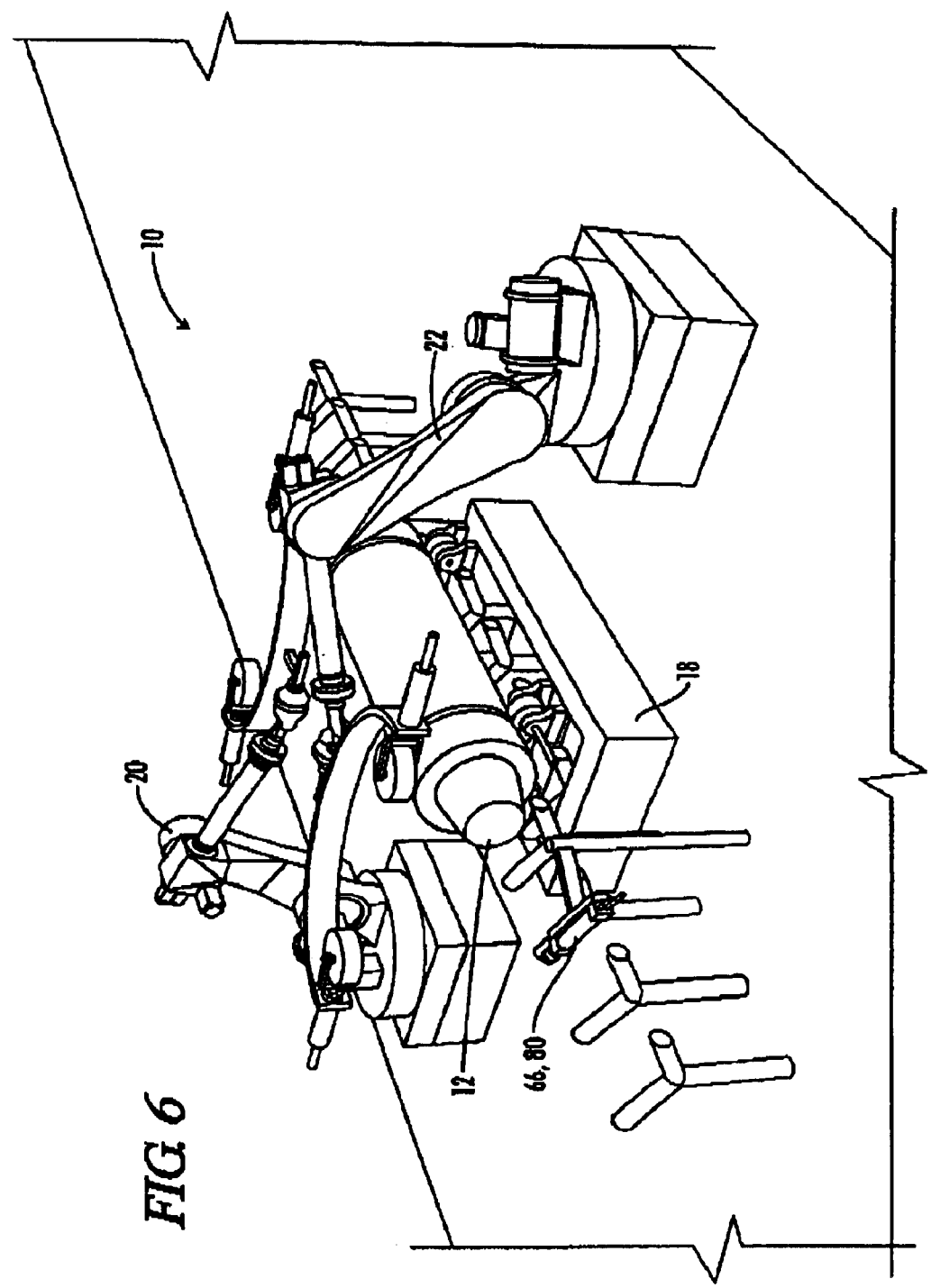
Figure 7:
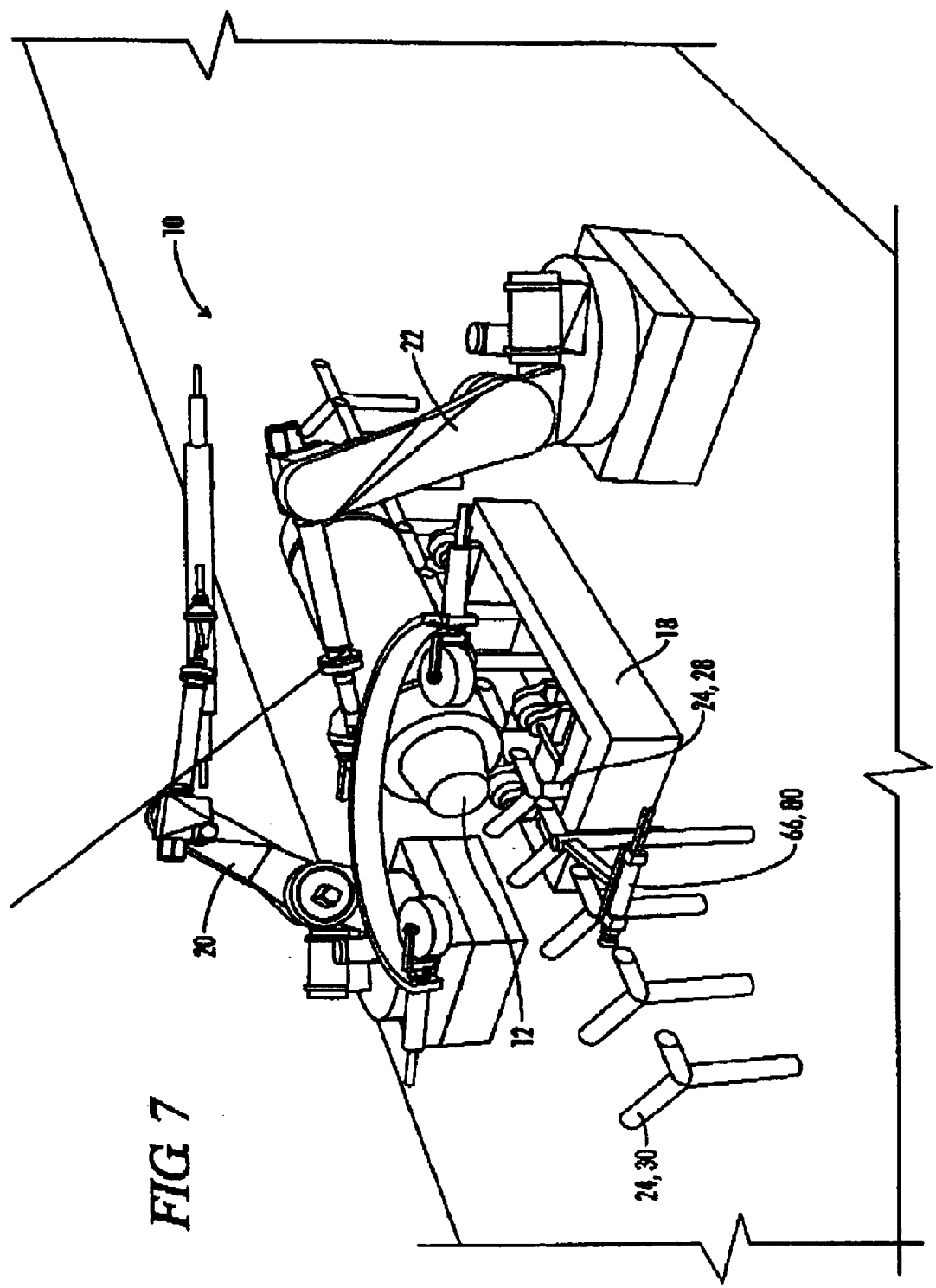

As seen in comparing the movement between the positions of FIGS. 3 and 4, the yoke 50 is pivotally attached to the robotic arm assembly 40 and is constructed such that the yoke 50 pivots downward over the electrode 12 when the robotic arm assembly moves to its operating position of FIG. 4.

As is also apparent in FIG. 4, when the robotic arm assemblies 40 of the master and slave robots 20 and 22 are received about the electrode 12, the yokes 50 of the master and slave robots 20 and 22 are spaced by a distance equal to about one half of a length of a portion of the electrode 12 which is to be inspected. Thus, after the two pairs of roller transducers are engaged with the electrode 12 as seen in FIG. 4, the electrode 12 will be rotated about its longitudinal axis by the powered rotational rollers 34A and 34B, while the robots 20 and 22 move their yokes 50 and their associated roller transducers along approximately one half the length of the electrode 12 simultaneously. Thus, the time for scanning an electrode 12 is reduced in half as compared to the time which would be required if only a single robot were utilized.

It will be appreciated, that the portion of the length 14 of the electrode 12 which is to be inspected will be substantially the entire length 14, but may not be exactly the entire length 14.

The inspection station 18 further includes an encoder 66 having an encoder head 67 arranged to axially engage the rearward end of the electrode 12 sensing a circumferential position of the electrode 12. Thus, the data gathered by the scanning operation can be correlated to a physical marker identifying a particular location around the circumference of a given electrode 12. The encoder 66 is constructed to be adjustable in elevation relative to the inspection station 18 to accommodate different diameters of electrodes 12.

Figure 2:
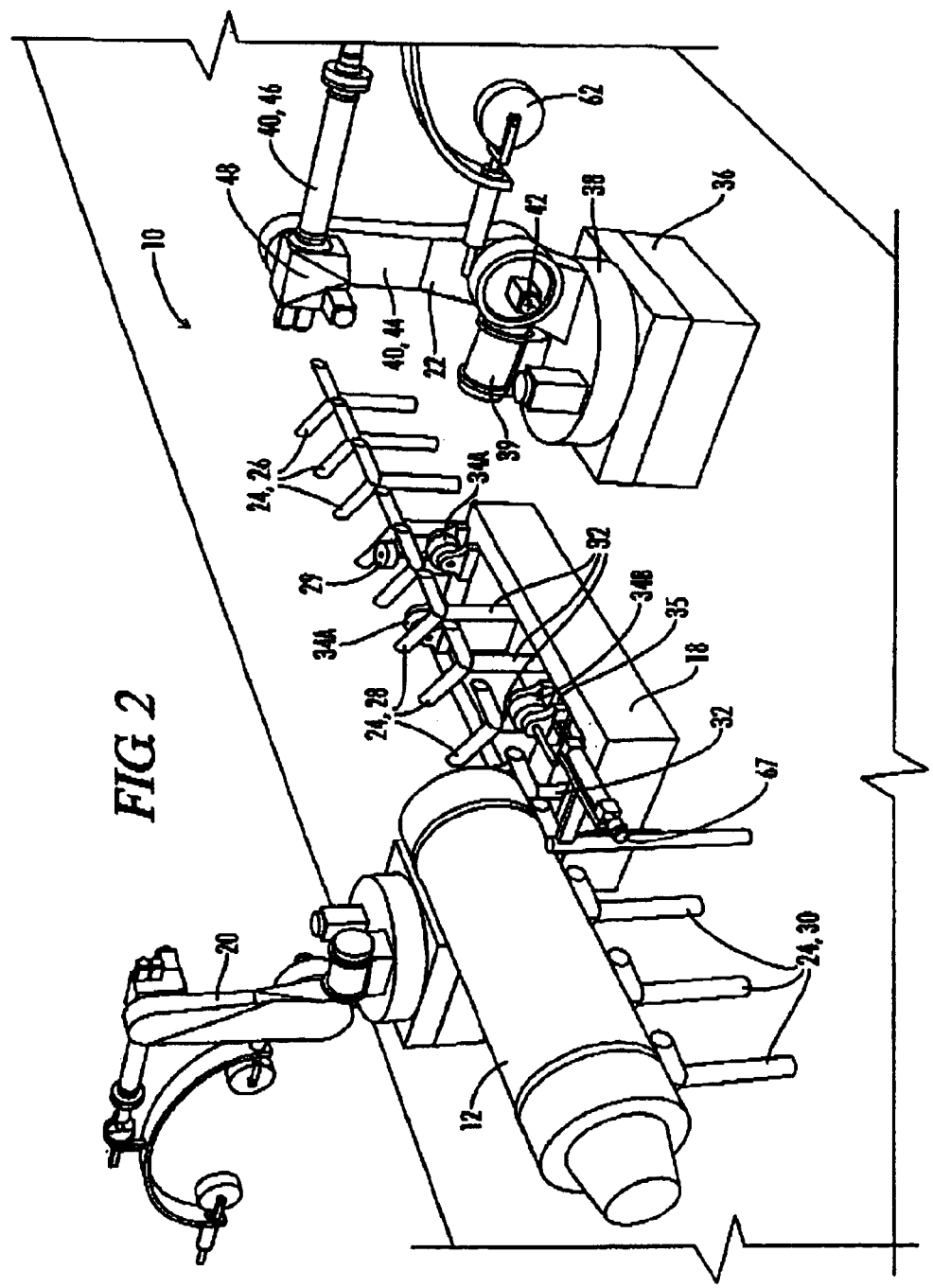
FIGS. 2–9 are a sequential series of schematic perspective views of the system of FIG. 1, showing a single carbon electrode as it moves into the inspection station and as it is then inspected, and as it subsequently moves out of the inspection station.

The encoder assembly 66 is used to provide a pickup of electrode circumferential position during testing. This assembly 66 is mounted on a pivot arm to permit swinging the encoder 66 from a withdrawn position as shown in FIG. 2 into the test position, as shown in FIG. 5. A motorized slide is provided to permit computer control of elevation of the encoder head 67 of the encoder assembly 66, so that it is centered on the end of the electrode 12. Software which will control the automatic adjustment of encoder assembly 66. The encoder 66 also includes a double acting air cylinder mechanism 80 to load and retract the encoder head 67 against the end of the electrode.

The transducers 60 and 62 are roller transducers which engage the exterior circumference of the electrode 12 and roll about their own axis as the electrode 12 is rotated by the powered rotational rollers 34. The transducers 60 and 62 are ultrasonic transducers, one of which will transmit a soundwave into the electrode 12 and the other of which will receive the soundwave after it is passed through the electrode 12. In general, the transducers 60 and 62 provide a system for measuring the velocity of sound through the electrode 12. Each pair of transducers 60 and 62 provide signals which when processed by appropriate software provide visual representations of the cross-sectional structure of the electrode 12 in the same manner in which a CAT-scan machine is utilized to take cross-sectional pictures of the human body. The data collected from the transducers 60 and 62 may also be utilized to create visual representations of the outer surface of the electrode 12. These various visual representations based upon measurements of sonic velocities through the carbon material making up the electrode 12 provide highly accurate representations of various physical defects, such as cracks contained within the electrode and on the surface thereof, and also show differing material densities throughout the cross-section and along the length of the electrode.

Figure 10:
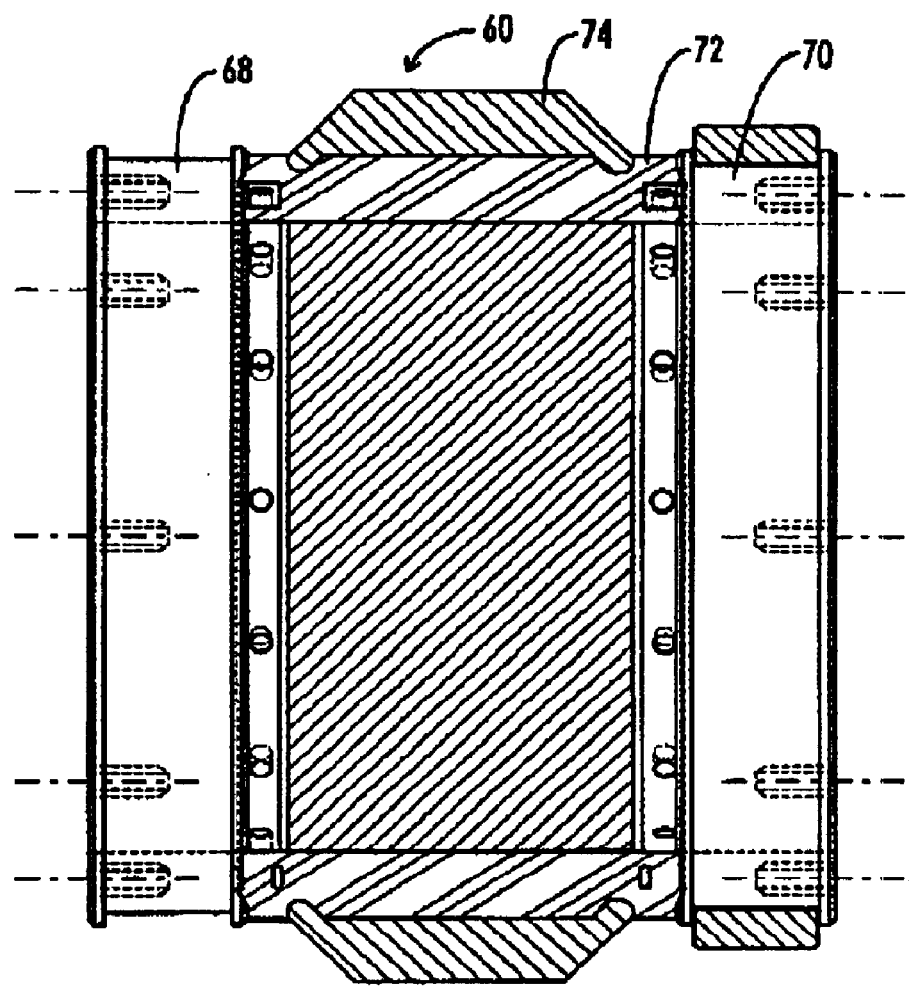
FIG. 10 is a cross-sectional view of the outer rim and rubber engagement member of the roller transducer.

In FIG. 10, one of the transducer rollers 60 is shown in cross-sectional view. First and second spaced stainless steel rims 68 and 70 support an inner rubber ring 72 upon which is mounted an outer replaceable rubber landing insert 74. The rubber landing inserts 74 have a thickness of from 3/16 to 1/4 inch, resulting in consistent compression of the center elastomer. This feature provides a fixed depth on the stainless steel rim assembly resulting in both longevity and consistency of performance. The two outer stainless steel rims 68 and 70 reduce the cost of resurfacing by providing a stable casting frame, and by increasing the number of times the roller may be resurfaced.

Figure 11:
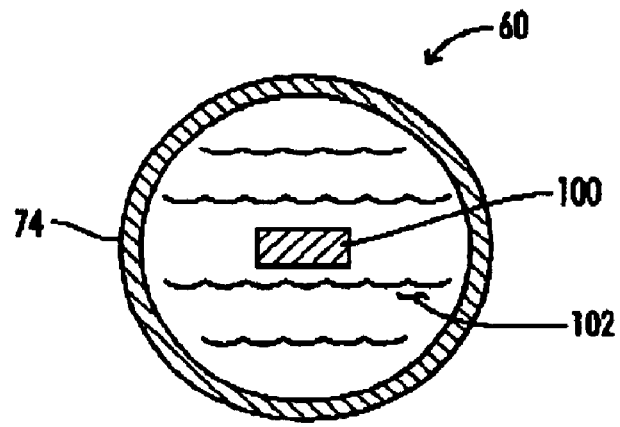
FIG. 11 is a schematic cross-sectional view of the roller transducer, at 90° to the view of FIG. 10, showing the prezo-electric transducer in an oil bath.

The internal details of roller transducer 60 are schematically illustrated in FIG. 11. Those internal details include a piezo-electric transducer 100 which is fixed relative to the external rims 68 and 70. Transducer 100 is in an oil bath 102 which conducts sound waves between transducer 100 and the insert 74 which engages electrode 12.

The pneumatic rams 56 and 58 are used to load the transducer wheels 60 and 62 against the electrode 12 with constant air pressure, and to retract the transducer wheels 60 and 62 away from the electrode 12 at the end of a scan. A manual air pressure regulator is provided to separately adjust each transducer wheel assembly.

As schematically shown in FIG. 1, the electronic signals gathered by the receiving side of each pair of transducers 60 and 62 are directed to a data acquisition instrumentation system 90. The data acquisition system 90 includes a Panametric model 5058PR high voltage pulser/receiver for each transducer pair, available from Panametrics, Inc. of Waltham, Mass. The system also includes a low noise 20 dB gain pre-amplifier mounted near the received side transducer of each pair. A power coupler is provided for each pair of transducers, and supplies voltage and receives RF signals from the associated pre-amplifier. A Panametric dual channel model 910 flaw detector receives the signals from the two power couplers.

Signals from the data acquisition system 90 are directed to a computer system 92, which is a single IBM compatible personal computer which is used for both control of the mechanisms of the apparatus 10 and for data analysis. The computer system preferably includes a 500 plus MHz Pentium processor operating on a Windows NT 4.0 operating system.

The computer system includes all software required for ultrasonic testing of electrodes 12 and integrates software for controlling the following functions of the system 10:

(1) rotator conveyor feed on/off control;

(2) rotator conveyor electrodes stop raise/lower controls;

(3) rotator conveyor elevator raise/lower control;

(4) rotator conveyor encoder pivot in/out inspection station;

(5) rotator encoder electrode diameter compensation raise/lower control;

(6) rotator encoder extend/retract air cylinder control;

(7) control of rotator support roller position to compensate for various length of electrodes;

(8) control of robot position orientation in polar coordinates relative to the terminal electrode centerline;

(9) control of rotator velocity and position; and

(10) control for the Model 9100 flaw detector.

The computer system provides a complete menu structure which supports operating the system safely in a production environment. Specific features include:

(1) operator log in;

(2) selection of part sizes from pre-set menus;

(3) system maintenance menu with clear system sensor status, (4) menu for specifying setup parameters, (5) menu with scan options, and (6) menu with analysis options organized for the operator.

Thus, it is seen that the apparatus and methods of the present invention readily achieve the ends and advantages mentioned as well as those inherent therein. Also the preferred embodiments of the invention have been illustrated and described for purposes of the present disclosure, numerous changes in the arrangement and construction of parts and steps may be made by those skilled in the art, which changes are encompassed within the scope and spirit of the present invention as defined by the appended claims.

What is claimed is:

1. An apparatus for inspection of a cylindrical carbon article having a length and a longitudinal axis parallel to the length, comprising:

an inspection station for receiving the article in a fixed longitudinal location and rotating the article about the longitudinal axis of the article while the article is in the fixed longitudinal location;

an encoder arranged to axially engage an end of the article for sensing a circumferential position of the article, the encoder being adjustable in elevation relative to the inspection station to accommodate different diameters of articles;

a master robot, including a first pair of transducers arranged to engage the article at circumferentially spaced positions about the article; and a slave robot constructed to move in synchronization with the master robot, including a second pair of transducers arranged to engage the article at a location longitudinally spaced from the first pair of transducers, so that the first and second pairs of transducers may simultaneously scan first and second portions, respectively, of the length of the article.

2. The apparatus of claim 1, wherein:

the transducers are ultrasonic transducers for measuring sound velocities through the article.

3. The apparatus of claim 1 wherein:

each of the robots includes a bi-furcated yoke having two arms with one of the transducers mounted on each arm.

4. The apparatus of claim 1, wherein:

the inspection station includes powered rotational rollers for rotating the article about the longitudinal axis of the article.

5. The apparatus of claim 4, wherein:

the powered rotational railers include first and second longitudinally spaced pairs powered rotational rollers, at least one of the pairs of powered rotational rollers being longitudinally movable to accommodate different lengths of articles.

6. The apparatus of claim 1, wherein:

the inspection station further includes an elevator for placing the article on the powered rotational rollers and for raising the article from the powered rotational rollers.

7. The apparatus of claim 1, further comprising:

a conveyor system having an article path in line with the longitudinal axis of the article at the inspection station.

8. An apparatus for inspection of a cylindrical carbon article having a length and a longitudinal axis parallel to the length, comprising:

an inspection station for receiving the article in a fixed longitudinal location and rotating the article about the longitudinal axis of the article while the article is in the fixed longitudinal location;

an encoder arranged to axially engage an end of the article for sensing a circumferential position of the article, the encoder being adjustable in elevation relative to the inspection station to accommodate different diameters of articles;

a master robot, including a first pair of transducers arranged to engage the article at circumferentially spaced positions about the article; and a slave robot constructed to move in synchronization with the master robot, including a second pair of transducers arranged to engage the article at a location longitudinally spaced from the first pair of transducers, so that the first and second pairs of transducers may simultaneously scan first and second portions; respectively, of the length of the article.

9. The apparatus of claim 8, wherein:

the transducers are ultrasonic transducers for measuring sound velocities through the article.

10. The apparatus of claim 8, wherein:

each of the robots includes a biurcated yoke having two arms with one of the transducers mounted on each arm.

11. The apparatus of claim 8, wherein:

the inspection station includes powered rotational rollers for rotating the article about the longitudinal axis of the article.

12. The apparatus of claim 11, wherein:

the powered rotational rollers include first and second longitudinally spaced pairs powered rotational rollers, at least one of the pairs of powered rotational rollers being longitudinally movable to accommodate different lengths of articles.

13. The apparatus of claim 8, wherein:

the inspection station further includes an elevator for placing the article on the powered rotational rollers and for raising the article from the powered rotational rollers.

14. The apparatus of claim 8, further comprising:

a conveyor system having an article path in line with the longitudinal axis of the article at the inspection station.

\* \* \* \* \*